United States Patent
Kubo et al.

(10) Patent No.: US 7,816,025 B2
(45) Date of Patent: Oct. 19, 2010

(54) ENZYME ELECTRODE, ENZYME ELECTRODE PRODUCING METHOD, SENSOR AND FUEL CELL EACH USING ENZYME ELECTRODE

(75) Inventors: Wataru Kubo, Inagi (JP); Tsuyoshi Nomoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 150 days.

(21) Appl. No.: 11/837,074

(22) Filed: Aug. 10, 2007

(65) Prior Publication Data
US 2008/0102323 A1   May 1, 2008

(30) Foreign Application Priority Data
Aug. 23, 2006   (JP) .............................. 2006-226699

(51) Int. Cl.
*H01M 4/00* (2006.01)
*C12M 1/40* (2006.01)

(52) U.S. Cl. ........................ 429/12; 204/403
(58) Field of Classification Search ............... 429/12, 429/218.1, 221, 231.1, 231.6; 204/403; 435/69.1
See application file for complete search history.

(56) References Cited

U.S. PATENT DOCUMENTS

| | | | | |
|---|---|---|---|---|
| 5,264,105 A | * | 11/1993 | Gregg et al. | 204/403.09 |
| 2002/0012943 A1 | * | 1/2002 | Fowlkes et al. | 435/7.1 |
| 2007/0056852 A1 | | 3/2007 | Kubo et al. | |
| 2007/0122689 A1 | | 5/2007 | Kubo et al. | |

FOREIGN PATENT DOCUMENTS

| | | |
|---|---|---|
| JP | 8-271472 A | 10/1996 |
| WO | 2006/009324 A1 | 1/2006 |

OTHER PUBLICATIONS

Qijin Chi et al., "Long-range Protein Electron Transfer Observed at the Single-molecule Level: In situ Mapping of Redox-gated Tunneling Resonance," Proceedings of the National Academy of Sciences of the United States of America, 2005, vol. 102, p. 16203-08.

Arthur Oubrie et al., "Crystal Structure of Quinohemoprotein Alcohol Dehydrogenase from Comamonas testosteroni," The Journal of Biological Chemistry, 2002, vol. 277, p. 3727-32.

Nicolas Mano et al., "Characteristics of a Miniature Compartmentless Glucose-O2 Biofuel Cell and Its Operation in a Living Plant" Journal of American Chemical Society, 2003, vol. 125, No. 21, pp. 6588-6594.

Kyoko Fujita et al., "Mimicking Protein-Protein Electron Transfer: Voltammetry of *Pseudomonas aeruginosa* Azurin and the *Thermus thermophilus* CuA Domain at w-Derivatized Self-Assembled-Monolayer Gold Electrodes" Journal of American Chemical Society, 2004, vol. 126, No. 43, pp. 13954-13961.

Christian Hammann et al., "Crystal Structures of Modified Apo-His117Gly and Apo-His46Gly Mutants of *Pseudomonas aeruginosa* Azurin" Journal of Molecular Biology, 1997, vol. 266, pp. 357-366.

* cited by examiner

*Primary Examiner*—Jennifer Michener
*Assistant Examiner*—Monique Wills
(74) *Attorney, Agent, or Firm*—Fitzpatrick, Cella, Harper & Scinto

(57) ABSTRACT

An amino acid capable of coordinately binding to a metallic complex is introduced to an active site within the enzyme or another controlled position near the active site. Therefore, when a mediator is introduced into the enzyme, a mediator-introduced position is controlled to be held at or near the active site.

5 Claims, 5 Drawing Sheets

SEQUENCE LISTING

```
<160> NUMBER OF SEQ ID NOS: 10

<210> SEQ ID NO 1
<211> LENGTH: 42
<212> TYPE: DNA
<213> ORGANISM: Artificial
<220> FEATURE:
<223> OTHER INFORMATION: PCR primer

<400> SEQUENCE: 1
```

```
aataatggat cccaacttac ccctaccttc tacgacaatt ca                    42
```

<210> SEQ ID NO 2
<211> LENGTH: 42
<212> TYPE: DNA
<213> ORGANISM: Artificial
<220> FEATURE:
<223> OTHER INFORMATION: PCR primer

<400> SEQUENCE: 2

```
aataatctcg agagagttgg agttcaccac cctacaattc aa                   42
```

<210> SEQ ID NO 3
<211> LENGTH: 948
<212> TYPE: DNA
<213> ORGANISM: Artificial
<220> FEATURE:
<223> OTHER INFORMATION: PCR product

<400> SEQUENCE: 3

```
aataatggat cccaacttac ccctaccttc tacgacaatt catgtcctaa tgtctctaac    60
atcgtacggg atactattgt caatgagcta agatcagacc ctcgtattgc cgcgagcatc   120
cttcgtcttc acttccacga ctgctttgtt aatggttgtg acgcatcgat cttgttagac   180
aacacaacat catttcgaac agagaaagat gcgtttggaa acgcaaactc ggcaagagga   240
tttccagtga ttgatagaat gaaagccgcg gtggagagtg catgcccaag aaccgtttca   300
tgcgcagatt tgctcaccat tgcagctcaa caatctgtca cttttgcggg aggtccttct   360
tggagagttc ctttgggcag aagagatagc ttacaagcat ttctggatct tgctaatgca   420
aatcttccag ctccattctt cacacttcca aacttaaag acagctttag aaatgttggc   480
ctcaaccgtt cttctgatct cgttgcactg tccgggggcc acacatttgg taaaaatcag   540
tgtcggttta ttatggacag attatacaac ttcagcaaca ccggtttacc cgatcctact   600
ctcaacacta cttatctcca aactcttcgt ggactatgtc ccctcaatgg taatctaagc   660
gctttggtgg attttgatct acgtacgcca acgattttg acaacaaata ctatgtgaat   720
ctcgaagagg aaaaaggact tatccaaagc gaccaagagt tgttctctag ccccaatgcc   780
actgacacaa tccctttggt gagatcattt gctaatagca cacaaacatt cttcaatgca   840
tttgtggagg cgatggatag gatgggaaac attacacctc ttacaggaac tcaaggacag   900
atcaggttga attgtagggt ggtgaactcc aactctctcg agattatt              948
```

<210> SEQ ID NO 4
<211> LENGTH: 308
<212> TYPE: PRT
<213> ORGANISM: Armoracia rusticana
<220> FEATURE:
<221> NAME/KEY: DOMAIN
<222> LOCATION: (1)..(308)
<223> OTHER INFORMATION: Horseradish peroxidase

<400> SEQUENCE: 4

```
Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
            20                  25                  30

Ala Ala Ser Ile Leu Arg Leu His Phe His Asp Cys Phe Val Asn Gly
        35                  40                  45

Cys Asp Ala Ser Ile Leu Leu Asp Asn Thr Thr Ser Phe Arg Thr Glu
    50                  55                  60
```

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
            85                  90                  95

Cys Ala Asp Leu Leu Thr Ile Ala Ala Gln Gln Ser Val Thr Leu Ala
                100                 105                 110

Gly Gly Pro Ser Trp Arg Val Pro Leu Gly Arg Arg Asp Ser Leu Gln
            115                 120                 125

Ala Phe Leu Asp Leu Ala Asn Ala Asn Leu Pro Ala Pro Phe Phe Thr
130                 135                 140

Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
                165                 170                 175

Cys Arg Phe Ile Met Asp Arg Leu Tyr Asn Phe Ser Asn Thr Gly Leu
                180                 185                 190

Pro Asp Pro Thr Leu Asn Thr Thr Tyr Leu Gln Thr Leu Arg Gly Leu
            195                 200                 205

Cys Pro Leu Asn Gly Asn Leu Ser Ala Leu Val Asp Phe Asp Leu Arg
210                 215                 220

Thr Pro Thr Ile Phe Asp Asn Lys Tyr Tyr Val Asn Leu Glu Glu Glu
225                 230                 235                 240

Lys Gly Leu Ile Gln Ser Asp Gln Glu Leu Phe Ser Ser Pro Asn Ala
                245                 250                 255

Thr Asp Thr Ile Pro Leu Val Arg Ser Phe Ala Asn Ser Thr Gln Thr
            260                 265                 270

Phe Phe Asn Ala Phe Val Glu Ala Met Asp Arg Met Gly Asn Ile Thr
                275                 280                 285

Pro Leu Thr Gly Thr Gln Gly Gln Ile Arg Leu Asn Cys Arg Val Val
            290                 295                 300

Asn Ser Asn Ser
305

<210> SEQ ID NO 5
<211> LENGTH: 308
<212> TYPE: PRT
<213> ORGANISM: Armoracia rusticana
<220> FEATURE:
<221> NAME/KEY: DOMAIN
<222> LOCATION: (1)..(308)
<223> OTHER INFORMATION: Horseradish peroxidase mutant

<400> SEQUENCE: 5

Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro His Ile
            20                  25                  30

Ala Ala Ser Ile Leu Arg Leu His Phe His Asp Cys Phe Val Asn Gly
            35                  40                  45

Cys Asp Ala Ser Ile Leu Leu Asp Asn Thr Thr Ser Phe Arg Thr Glu
        50                  55                  60

Lys Asp Ala Phe Gly Asn Ala Asn His Ala Arg Gly Phe Pro Val Ile
65                  70                  75                  80

Asp Arg Met Lys Ala Ala Val Glu Ser Ala Cys Pro Arg Thr Val Ser
            85                  90                  95

-continued

```
Cys Ala Asp Leu Leu Thr Ile Ala Ala Gln Gln Ser Val Thr Leu Ala
            100                 105                 110
Gly Gly Pro Ser Trp Arg Val Pro Leu Gly Arg Arg Asp Ser Leu Gln
        115                 120                 125
Ala Phe Leu Asp Leu Ala Asn Ala Asn Leu Pro Ala Pro Phe Phe Thr
    130                 135                 140
Leu Pro Gln Leu Lys Asp Ser Phe Arg Asn Val Gly Leu Asn Arg Ser
145                 150                 155                 160
Ser Asp Leu Val Ala Leu Ser Gly Gly His Thr Phe Gly Lys Asn His
                165                 170                 175
Cys Arg Phe Ile Met Asp Arg Leu Tyr Asn Phe Ser Asn Thr Gly Leu
            180                 185                 190
Pro Asp Pro Thr Leu Asn Thr Thr Tyr Leu Gln Thr Leu Arg Gly Leu
        195                 200                 205
Cys Pro Leu Asn Gly Asn Leu Ser Ala Leu Val Asp Phe Asp Leu Arg
    210                 215                 220
Thr Pro Thr Ile Phe Asp Asn Lys Tyr Tyr Val Asn Leu Glu Glu Glu
225                 230                 235                 240
Lys Gly Leu Ile Gln Ser Asp Gln Glu Leu Phe Ser Ser Pro Asn Ala
                245                 250                 255
Thr Asp Thr Ile Pro Leu Val Arg Ser Phe Ala Asn Ser Thr Gln Thr
            260                 265                 270
Phe Phe Asn Ala Phe Val Glu Ala Met Asp Arg Met Gly Asn Ile Thr
        275                 280                 285
Pro Leu Thr Gly Thr Gln Gly Gln Ile Arg Leu Asn Cys Arg Val Val
    290                 295                 300
Asn Ser Asn Ser
305

<210> SEQ ID NO 6
<211> LENGTH: 45
<212> TYPE: DNA
<213> ORGANISM: Artificial
<220> FEATURE:
<223> OTHER INFORMATION: PCR primer

<400> SEQUENCE: 6
aataatcata tggcctacct gcctgcccaa cagattgatg tccag            45

<210> SEQ ID NO 7
<211> LENGTH: 42
<212> TYPE: DNA
<213> ORGANISM: Artificial
<220> FEATURE:
<223> OTHER INFORMATION: PCR primer

<400> SEQUENCE: 7
aataatcggc cgctaggcac ttttggcata gtcatccaaa at                42

<210> SEQ ID NO 8
<211> LENGTH: 1791
<212> TYPE: DNA
<213> ORGANISM: Artificial
<220> FEATURE:
<223> OTHER INFORMATION: PCR product

<400> SEQUENCE: 8
aataatcata tggcctacct gcctgcccaa cagattgatg tccagtctag tcttctcagt    60
gaccctagca aggttgcagg aaagacctat gattacatca ttgctggtgg tggtttgact   120
```

```
ggccttactg ttgctgccaa attgacagaa aaccccaaga tcaaagtcct ggtcattgaa      180
aagggcttct atgagtccaa cgatggagcc atcatcgagg atccaaatgc ttatggacaa      240
atctttggca ccactgttga ccagaactac ctcaccgttc ccctgatcaa caaccgcacg      300
aacaatatca aggccggtaa aggtcttgga ggatcaacct tgataaacgg tgactcctgg      360
actcgcccag acaaagtcca gattgattct tgggagaagg tctttggcat ggaaggttgg      420
aattgggaca acatgttcga gtacatgaag aaggccgagg ctgcacgtac ccctactgct      480
gctcagcttg ctgctggcca ctccttcaat gctacctgcc atggaaccaa cggtactgtt      540
caatccggag cccgtgacaa cggccagcct tggtctccta ttatgaaggc ccttatgaac      600
accgtctcgg cccttggtgt ccccgtacag caagactttc tctgtggtca tcctcgaggt      660
gtctctatga tcatgaacaa tctcgacgaa aaccaagttc gtgttgatgc tgcccgtgca      720
tggctgcttc ccaactacca gcgctcgaat ttggagatcc ttactggtca gatggttgga      780
aaggttctgt ttaaacagac cgcatccggt ccccaggctg ttggtgtgaa cttcggtact      840
aataaggccg tcaactttga cgtctttgct aagcatgagg tccttttggc tgctggctca      900
gctatctctc cgctgatctt ggaatattct ggcataggct tgaagtctgt tcttgatcaa      960
gccaatgtca ctcagcttct tgatcttcct gttggtatca atatgcaaga tcagaccaca     1020
accactgtca gttcccgtgc tagttccgct ggtgctggtc agggtcaggc cgtcttcttc     1080
gccaatttca ctgagacctt cggtgactac gccccccagg ccaggcactt actcaacacc     1140
aagctcgacc aatgggccga ggagaccgtt gcgcgcggtg gtttccataa tgtaactgct     1200
ctcaaagtac aatacgaaaa ctatcgtaac tggctccttg acgaagacgt cgccttcgcc     1260
gagcttttca tggacaccga gggcaagatc aacttcgatt tatgggatct catccctttc     1320
actcgtggtt ccgtccatat cctcagtagc gatccttacc tatggcaatt cgccaacgac     1380
cccaaattct tcctgaacga gtttgacctc cttggtcaag ctgccgcttc caagcttgct     1440
cgtgatctca ctagccaagg cgctatgaag gagtacttcg ccggggagac tcttccagga     1500
tacaacttgg tccagaatgc tactctttcc cagtggtcgg attatgtctt acagaacttc     1560
cgtcccaact ggcatgctgt gagcagctgc tctatgatgt ctagagagct tggtggtgtc     1620
gttgatgcta ctgccaaggt gtacggtacc caaggcctac gtgtcattga cgggtctatt     1680
cctccgactc aggtgtcttc ccatgtcatg accattttct acggaatggc tttgaaggtt     1740
gctgatgcca ttttggatga ctatgccaaa agtgcctagc ggccgattat t              1791
```

<210> SEQ ID NO 9
<211> LENGTH: 587
<212> TYPE: PRT
<213> ORGANISM: Penicillium amagasakiense
<220> FEATURE:
<221> NAME/KEY: DOMAIN
<222> LOCATION: (1)..(587)
<223> OTHER INFORMATION: glucose oxidase

<400> SEQUENCE: 9

Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly

-continued

```
            50                  55                  60
Ala Ile Ile Glu Asp Pro Asn Ala Tyr Gly Gln Ile Phe Gly Thr Thr
 65                  70                  75                  80

Val Asp Gln Asn Tyr Leu Thr Val Pro Leu Ile Asn Asn Arg Thr Asn
                 85                  90                  95

Asn Ile Lys Ala Gly Lys Gly Leu Gly Gly Ser Thr Leu Ile Asn Gly
                100                 105                 110

Asp Ser Trp Thr Arg Pro Asp Lys Val Gln Ile Asp Ser Trp Glu Lys
                115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
                180                 185                 190

Leu Met Asn Thr Val Ser Ala Leu Gly Val Pro Val Gln Gln Asp Phe
                195                 200                 205

Leu Cys Gly His Pro Arg Gly Val Ser Met Ile Met Asn Asn Leu Asp
210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
                260                 265                 270

Phe Gly Thr Asn Lys Ala Val Asn Phe Asp Val Phe Ala Lys His Glu
                275                 280                 285

Val Leu Leu Ala Ala Gly Ser Ala Ile Ser Pro Leu Ile Leu Glu Tyr
                290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
                340                 345                 350

Val Phe Phe Ala Asn Phe Thr Glu Thr Phe Gly Asp Tyr Ala Pro Gln
                355                 360                 365

Ala Arg Asp Leu Leu Asn Thr Lys Leu Asp Gln Trp Ala Glu Glu Thr
370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Lys Ile Asn Phe Asp Leu Trp Asp Leu
                420                 425                 430

Ile Pro Phe Thr Arg Gly Ser Val His Ile Leu Ser Ser Asp Pro Tyr
                435                 440                 445

Leu Trp Gln Phe Ala Asn Asp Pro Lys Phe Phe Leu Asn Glu Phe Asp
                450                 455                 460

Leu Leu Gly Gln Ala Ala Ala Ser Lys Leu Ala Arg Asp Leu Thr Ser
465                 470                 475                 480
```

```
Gln Gly Ala Met Lys Glu Tyr Phe Ala Gly Glu Thr Leu Pro Gly Tyr
                485                 490                 495

Asn Leu Val Gln Asn Ala Thr Leu Ser Gln Trp Ser Asp Tyr Val Leu
            500                 505                 510

Gln Asn Phe Arg Pro Asn Trp His Ala Val Ser Ser Cys Ser Met Met
        515                 520                 525

Ser Arg Glu Leu Gly Gly Val Val Asp Ala Thr Ala Lys Val Tyr Gly
    530                 535                 540

Thr Gln Gly Leu Arg Val Ile Asp Gly Ser Ile Pro Pro Thr Gln Val
545                 550                 555                 560

Ser Ser His Val Met Thr Ile Phe Tyr Gly Met Ala Leu Lys Val Ala
                565                 570                 575

Asp Ala Ile Leu Asp Asp Tyr Ala Lys Ser Ala
                580                 585

<210> SEQ ID NO 10
<211> LENGTH: 587
<212> TYPE: PRT
<213> ORGANISM: Penicillium amagasakiense
<220> FEATURE:
<221> NAME/KEY: DOMAIN
<222> LOCATION: (1)..(587)
<223> OTHER INFORMATION: glucose oxidase mutant

<400> SEQUENCE: 10

Tyr Leu Pro Ala Gln His Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu His Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser His Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
    130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
    210                 215                 220

Glu Asn Gln Val Arg Val His Ala Ala Arg Ala Trp Leu Leu Pro Asn
225                 230                 235                 240
```

```
Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
    290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
    370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Lys Ile Asn Phe Asp Leu Trp Asp Leu
            420                 425                 430

Ile Pro Phe Thr Arg Gly Ser Val His Ile Leu Ser Ser Asp Pro Tyr
        435                 440                 445

Leu Trp Gln Phe Ala Asn Asp Pro Lys Phe Phe Leu Asn Glu Phe Asp
    450                 455                 460

Leu Leu Gly Gln Ala Ala Ala Ser Lys Leu Ala Arg Asp Leu Thr Ser
465                 470                 475                 480

Gln Gly Ala Met Lys Glu Tyr Phe Ala Gly Glu Thr Leu Pro Gly Tyr
                485                 490                 495

Asn Leu Val Gln Asn Ala Thr Leu Ser Gln Trp Ser Tyr Val Leu
            500                 505                 510

Gln Asn Phe Arg Pro Asn Trp His Ala Val Ser Ser Cys Ser Met Met
        515                 520                 525

Ser Arg Glu Leu Gly Gly Val Val Asp Ala Thr Ala Lys Val Tyr Gly
    530                 535                 540

Thr Gln Gly Leu Arg Val Ile Asp Gly Ser Ile Pro Pro Thr Gln Val
545                 550                 555                 560

Ser Ser His Val Met Thr Ile Phe Tyr Gly Met Ala Leu Lys Val Ala
                565                 570                 575

Asp Ala Ile Leu Asp Asp Tyr Ala Lys Ser Ala
            580                 585
```

ENZYME ELECTRODE, ENZYME ELECTRODE PRODUCING METHOD, SENSOR AND FUEL CELL EACH USING ENZYME ELECTRODE

BACKGROUND OF THE INVENTION

1. Field of the Invention

The present invention relates to an enzyme electrode and a method of producing the enzyme electrode.

2. Description of the Related Art

An oxidation-reduction (redox) enzyme transfers electrons between a substrate and a cofactor when the enzyme reacts with the substrate. Therefore, a sensor and a fuel cell utilizing the feature of the enzyme can be realized if those electrons can be transferred to an electrically conductive member.

In many cases, a redox center of the redox enzyme is deeply positioned inside a protein having a three dimensional structure (the redox center is also called an active location or an active site). For that reason, it is generally difficult to efficiently detect electron transfer between the active site and the conductive member.

To overcome such a difficulty, a method has been developed which electrically connects the enzyme and the conductive member by a material called a mediator. The mediator is able to enter the inside of the protein constituting the enzyme. Therefore, when the mediator is positioned near the active site, charges generated during a redox reaction can be transferred to the conductive member through the mediator. In other words, charges generated by an enzyme reaction are detected through the conductive member as a result of diffusion of the mediator taking part in the transfer of electrons with respect to the active site or electron hopping between the mediators.

Japanese Patent Laid-Open No. 8-271472 discloses a technique of introducing ferrocene, which functions as a mediator, to a main body or a side chain of the enzyme by utilizing a covalent bond.

However, the mediator introduced to the enzyme by the technique disclosed in Japanese Patent Laid-Open No. 8-271472 is not controlled with respect to the position to which it is introduced. Hence, the mediator is introduced to a random position within the enzyme.

When the mediator is introduced in such a manner, efficient transfer of charges from the active site is not expected except for the case that ferrocene is casually positioned near the active site. In particular, when the disclosed technique is applied to an enzyme sensor, the concentration of a substrate, i.e., the concentration of a target material to be measured, is required to be exactly sensed and a further improvement is demanded.

SUMMARY OF THE INVENTION

The present invention is directed to a technique of, when a mediator is introduced to an enzyme, controlling a mediator-introduced position to be located near an active site.

According to a first aspect of the present invention, an enzyme electrode comprises an enzyme, an electrically conductive member to which the enzyme is immobilized, a metallic complex electrically connected to the electrically conductive member, and an amino acid arranged at an active site within the enzyme or at a controlled position near the active site and coordinately bound to the metallic complex.

According to a second aspect of the present invention, an enzyme electrode producing method comprises the steps of preparing an electrically conductive member to which a metallic complex is immobilized, recombining a gene coding an enzyme by a genetic engineering operation, thus arranging an amino acid at an active site within the enzyme or at a controlled position near the active site, and coordinately binding the amino acid and the metallic complex to each other.

Further features of the present invention will become apparent from the following description of exemplary embodiments with reference to the attached drawings.

DESCRIPTION OF THE EMBODIMENTS

First Embodiment

Enzyme Electrode

Figure 1:
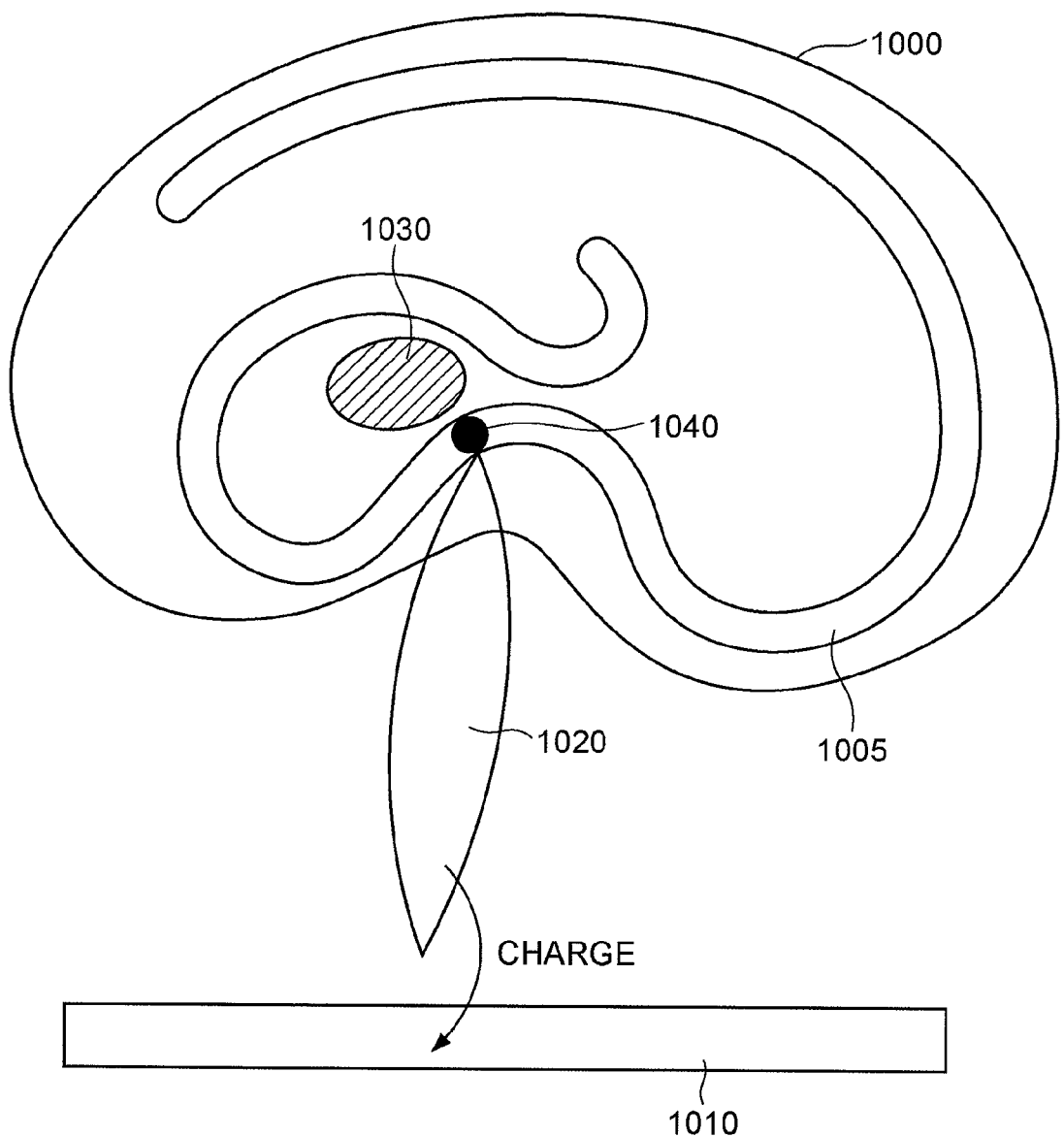
FIG. 1 is an illustration for explaining an enzyme electrode according to a first embodiment of the present invention.

FIG. 1 is a conceptual illustration showing an enzyme electrode according to a first embodiment of the present invention.

Referring to FIG. 1, the enzyme electrode includes an enzyme 1000, an electrically conductive member 1010 to which the enzyme 1000 is immobilized, a metallic complex 1020 electrically connected to the conductive member 1010, and an active site 1030 within the enzyme. Reference numeral 1040 denotes an amino acid arranged at or near the active site 1030 within the enzyme. Numeral 1005 denotes a protein which constitutes the enzyme and is partly modified.

In the first embodiment, the amino acid bound to the metallic complex, which functions as a mediator, is previously arranged at or near the active site within the enzyme. The amino acid and the metallic complex chemically bind with each other. Consequently, a position of the mediator relative to the active site can be controlled.

1) Amino Acid and Enzyme

The amino acid arranged at or near the active site within the enzyme will be described first.

The above-described arrangement of the amino acid is realized, for example, by introducing, in an enzyme expression system which employs a gene recombinant bacterium, a site specific variation to a recombinant gene of the enzyme with a gene engineering method.

Herein, the term "near the active site" means that, in an oxidation-reduction (redox) enzyme, an atom is positioned within a distance of 1.6 nm, preferably 1.29 nm, from the atom which constitutes a substrate, a prosthetic group or a cofactor of the enzyme subjected to oxidation or reduction, and which takes part in the oxidation or the reduction. The position of the active site is determined by an X-ray crystal analysis or a nuclear magnetic resonance spectrum analysis. For example, when the enzyme is glucose oxidase, flavin adenine dinucleotide serves as the active site. When the enzyme is peroxidase of *Armoracia rusticana*, heme serves as the active site. When the enzyme is laccase, a copper atom serves as the active site. The term "atom taking part in the oxidation or the reduction" means an atom which particularly takes part in the oxidation or the reduction among atoms located at the active site. For example, when the active site is flavin adenine dinucleotide, nitrogen atoms at 1- and 10-positions of a flavin ring correspond to the relevant atom. When the active site is nicotinamide adenine dinucleotide, a carbon atom at the 4-position of nicotinamide corresponds to the relevant atom. When the active site is pyrroloquinoline quionone, oxygen atoms at 4- and 5-positions correspond to the relevant atom. When the active site is heme, an iron atom corresponds to the relevant atom. The distance of 1.6 nm, preferably 1.29 nm, is based on the following two reports. One report says that if a distance from the active center of protein exceeds 1.6 nm, an electron transfer speed is drastically reduced (Qijin Chi, et al., "Proceedings of the National Academy of Sciences of the United States of America", 2005, Vol. 102, p. 16203). The other report says that an electron transfer distance of 1.29 nm is one of the longest distances so far determined as physiological distances between two redox centers (Arthur Oubrie, et al., "The Journal of Biological Chemistry", 2002, Vol. 277, p. 3727).

One example of the amino acid is histidine.

EXAMPLE 1, described in detail later, represents the case where peroxidase of *Armoracia rusticana* is used as the enzyme and histidine is arranged near heme which serves as the active site of the *Armoracia rusticana* peroxidase.

EXAMPLE 2, described in detail later, represents the case where glucose oxidase is used as the enzyme and histidine is arranged near flavin adenine dinucleotide (FAD) which serves as the active site of the glucose oxidase.

As the enzyme used in the first embodiment, other general redox enzymes, including bilirubin oxidase, laccase, and thioredoxin reductase, are also usable in addition to the *Armoracia rusticana* peroxidase and glucose oxidase.

The amino acid arranged at or near the active site within the enzyme is not limited to a particular one so long as it is capable of binding to the metallic complex by a coordinate bond. For example, the amino acid can be histidine or cystine, or a non-natural amino acid having a coordination ability with respect to a metal center.

The term "active site" used in the first embodiment means a site at which charges are transferred within the enzyme. For example, the active site is a redox center or a site receiving charges from the redox center.

The redox center includes the following two concepts.

One type of redox center is held within the enzyme like FAD of glucose oxidase, and the other type is basically not held within the enzyme like nicotinamide adenine dinucleotide ($NAD^+$) of glucose dehydrogenase.

The position to which the amino acid is artificially introduced can be a position where the amino acid indirectly contacts the active site through the protein constituting the enzyme, or a position spaced from the active site by a predetermined distance so long as the amino acid is located nearby. If necessary, it is also possible to introduce, into the enzyme, another amino acid bound to another metallic complex which serves as a relay for transporting, to the electrode, charges from the metallic complex bound to the amino acid which is arranged at or near the active site.

2) Metallic Complex

Examples of the metallic complex usable in the first embodiment are as follows.

A metal center of the metallic complex can be, e.g., iron, cobalt, ruthenium, osmium, or chromium. A ligand of the metallic complex can be, e.g., a heterocyclic compound such as bipyridine, terpyridine or imidazole, cyclopentadienyl, or a derivative thereof. The metallic complex is desirably able to perform fast transfer of charges between itself and the conductive member. To meet such a demand, the metallic complex can contain, for example, a π-conjugate molecule as the ligand. The center metal of the metallic complex can be single or plural. When the center metal is plural, the metals can be the same or different elements. When the metallic complex contains plural kinds of elements, it is important to arrange the elements in consideration of the potential relationship between the different metal centers so that electrons are transported in the desired direction.

Furthermore, the metallic complex can be coordinately bound to the amino acid, such as histidine, when the metallic complex has a leaving group. Examples of the leaving group include halogen, boron tetrafluoride, and phosphorous hexafluoride.

When the metallic complex is bound to the conductive member, the distance between the enzyme and the conductive member can be controlled by changing the molecular length of the metallic complex. With such control of the molecular length, the following two factors can be balanced. Namely, (a) charge transport rate from the active site of the enzyme to the conductive member can be increased by reducing the molecular length, and (b) activity of the enzyme can be kept from being reduced due to an interaction with the conductive member by increasing the molecular length. The molecular length can be practically changed by a method of modifying molecular design of the ligand or a method of increasing the number of stages of a polynuclear complex.

3) Electrically Conductive Member

The electrically conductive member can be constituted, for example, as a metallic electrode of, e.g., gold or platinum, a carbon electrode, or an indium tin oxide electrode.

The metallic complex and the conductive member are just required to be electrically connected to each other. For example, the metallic complex and the conductive member can be electrically connected to each other through some material interposed between them or directly without interposition of any material. Further, they can be physically and/or chemically bound as required.

When the enzyme is immobilized to the conductive member, the enzyme can be held in direct contact with the conductive member, or can be immobilized to the conductive member through the metallic complex. As an alternative, the immobilization of the enzyme can also be practically realized by using a polymer or a bridging agent which has a reactive functional group.

Although the mediator can be introduced only at a random position within the enzyme in the related art, the mediator-introduced position can be substantially controlled according to the first embodiment described above.

Second Embodiment

Enzyme Electrode Producing Method

Figure 2:
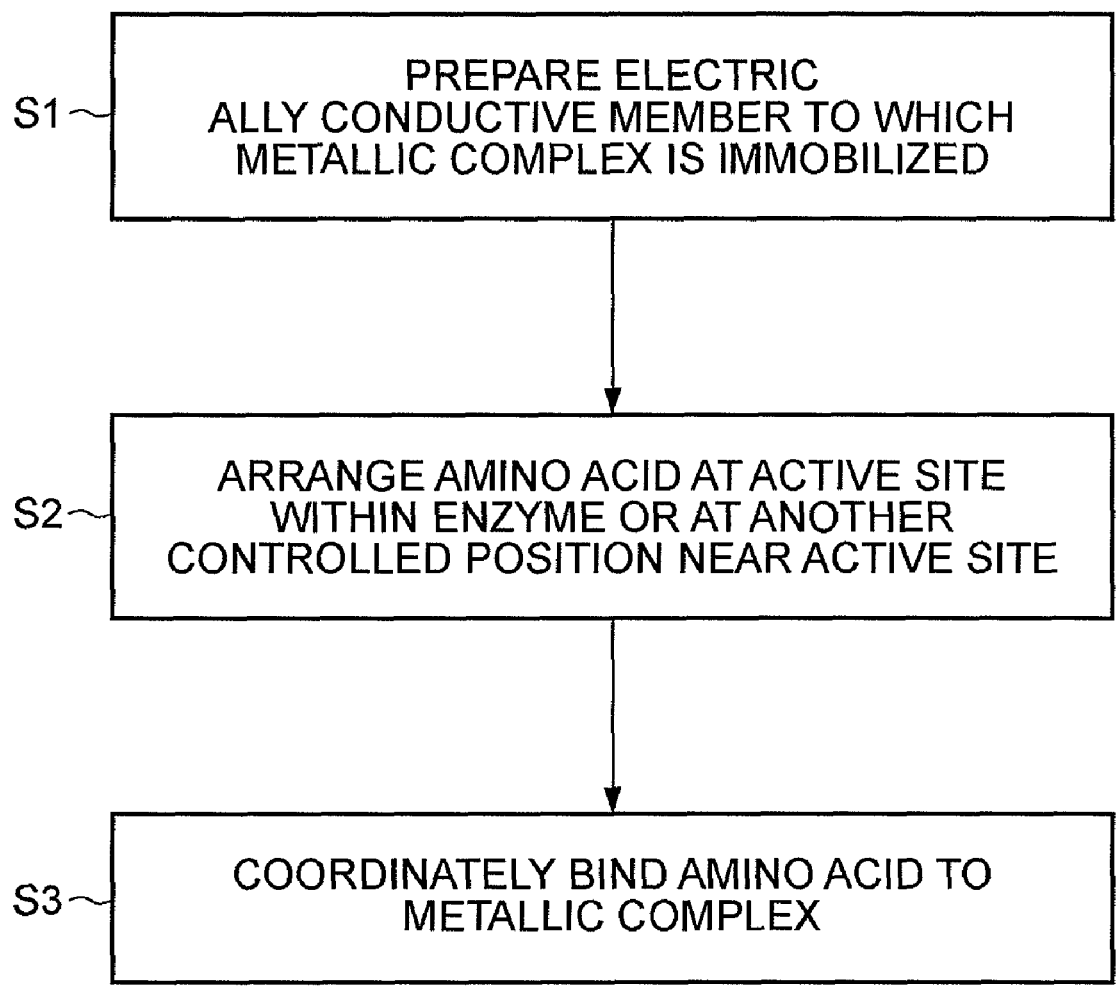
FIG. 2 is a flowchart for explaining steps of producing the enzyme electrode according to a first embodiment of the present invention.

A method of producing the enzyme electrode according to a second embodiment will be described next with reference to FIG. 2.

An electrically conductive member including a metallic complex immobilized thereto is first prepared (S1).

More specifically, the conductive member is prepared in step S1, by way of example, as follows.

First, an electrically conductive member is prepared by a method of using an electrically conductive material as it is, or a method of forming an electrically conductive layer on an insulating material of, e.g., glass or a polymer. The method of forming the conductive layer can be practiced, for example, by vapor deposition, sputtering, or printing.

Next, the metallic complex is immobilized to the conductive member. The immobilization of the metallic complex can be practiced by one of the following two methods; i.e., (1) a method of contacting, with the conductive member, a solution of the metallic complex which has, as a functional group of a ligand, a group capable of binding to the conductive member or a material immobilized to the surface of the conductive member, and (2) a method of contacting, with the conductive member, a solution of a ligand which has a functional group capable of binding to the conductive member or a material immobilized to the surface of the conductive member, thus immobilizing the ligand, and then contacting, with the conductive member, a solution of a compound which contains a center metal of the metallic complex having a leaving group.

Next, a gene coding an enzyme is recombined by a genetic engineering operation so that an amino acid is arranged at an active site within the enzyme or another controlled position near the active site (S2).

More specifically, a codon coding the objective amino acid is substituted for or inserted to the amino acid which is contained in the gene coding the enzyme and which is located near the active site. To arrange histidine at a controlled position, for example, CAT or CAC which is a codon coding histidine is substituted for or inserted to a codon coding the amino acid which is located near the active site within the enzyme. By arranging the amino acid in such a manner while artificially controlling the position of the substituted or inserted codon, the metallic complex can be finally arranged near the active site.

Regarding the operation of artificially introducing the amino acid into the enzyme while controlling the position of the introduced amino acid, the technical matters described in the first embodiment are similarly employed in this second embodiment as well.

Next, the amino acid is coordinately bound to the metallic complex (S3).

More specifically, the coordinate binding of the amino acid is performed, for example, by contacting a solution of the enzyme with the electric conductive member to which the metallic complex having the leaving group has been immobilized.

The enzyme electrode is thus obtained.

Third Embodiment

Sensor

A sensor constituted by using the enzyme electrode described above in the first embodiment will be described with reference to FIG. 3.

Figure 3:
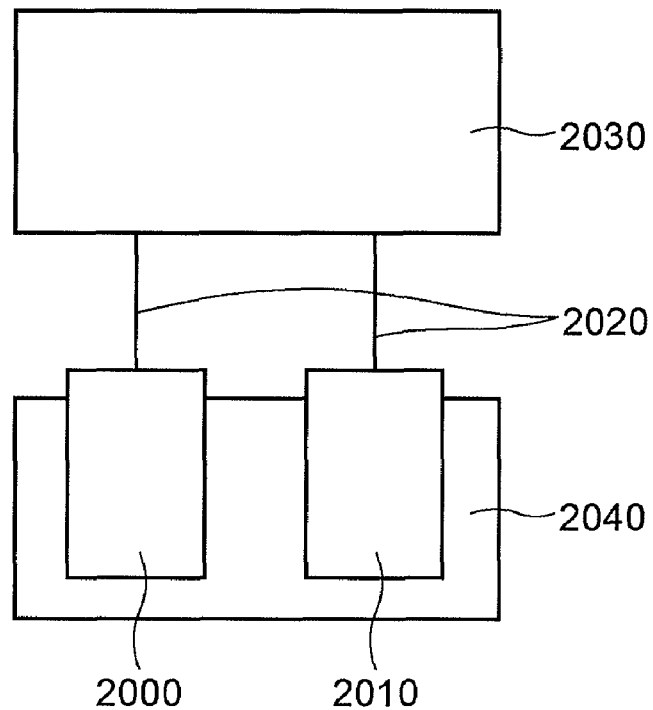
FIG. 3 is a schematic view for explaining a sensor according to a third embodiment of the present invention.

Referring to FIG. 3, the sensor includes an enzyme electrode 2000 and a counter electrode 2010 which are connected to an external apparatus 2030 through leads 2020. The enzyme electrode and the counter electrode are disposed in an electrolyte 2040.

As required, a reference electrode and/or a mechanism for holding the electrolyte can also be employed.

By measuring an electric signal taken out by the external apparatus 2030 through the enzyme electrode in the above-described arrangement, it is possible to examine the presence/absence and the concentration of a material which is contained in the electrolyte and is to be detected. A sensor utilizing the enzyme electrode is thus realized. The electric signal can be measured in the form of a current, a charge amount, a voltage, a potential, or impedance. Further, a potential or a voltage, for example, can be applied to the enzyme electrode from the external apparatus. By storing the relationship between the electric signal and the concentration of a particular substrate, for example, in a database beforehand, the obtained signal can be compared with information stored in the database.

Fourth Embodiment

Fuel Cell

A fuel cell constituted by using the enzyme electrode described above in the first embodiment will be described with reference to FIG. 4.

Figure 4:
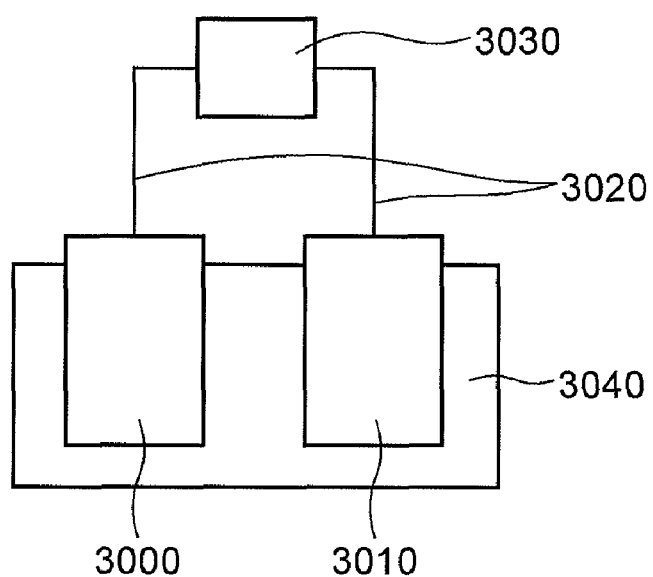
FIG. 4 is an illustration for explaining a fuel cell according to a fourth embodiment of the present invention.

Referring to FIG. 4, the fuel cell includes an anode 3000 and a cathode 3010. The enzyme electrode is used as at least one of the anode and the cathode. The anode and the cathode are connected to a load 3030 through leads 3020.

The anode and the cathode are disposed in an electrolyte 3040. As required, a mechanism for holding the electrolyte can also be employed. When fuel is present in the electrolyte, voltage is generated between the anode and the cathode so that a current flows to the load, thus implementing work.

The term "load" used herein means, for example, a pump for supplying drugs or a transmitter for transmitting an electric signal.

EXAMPLES

The present invention will now be described in detail in connection with EXAMPLES. Note that the enzyme electrode producing method of the present invention is not limited to following EXAMPLES.

Example 1

Figure 5:
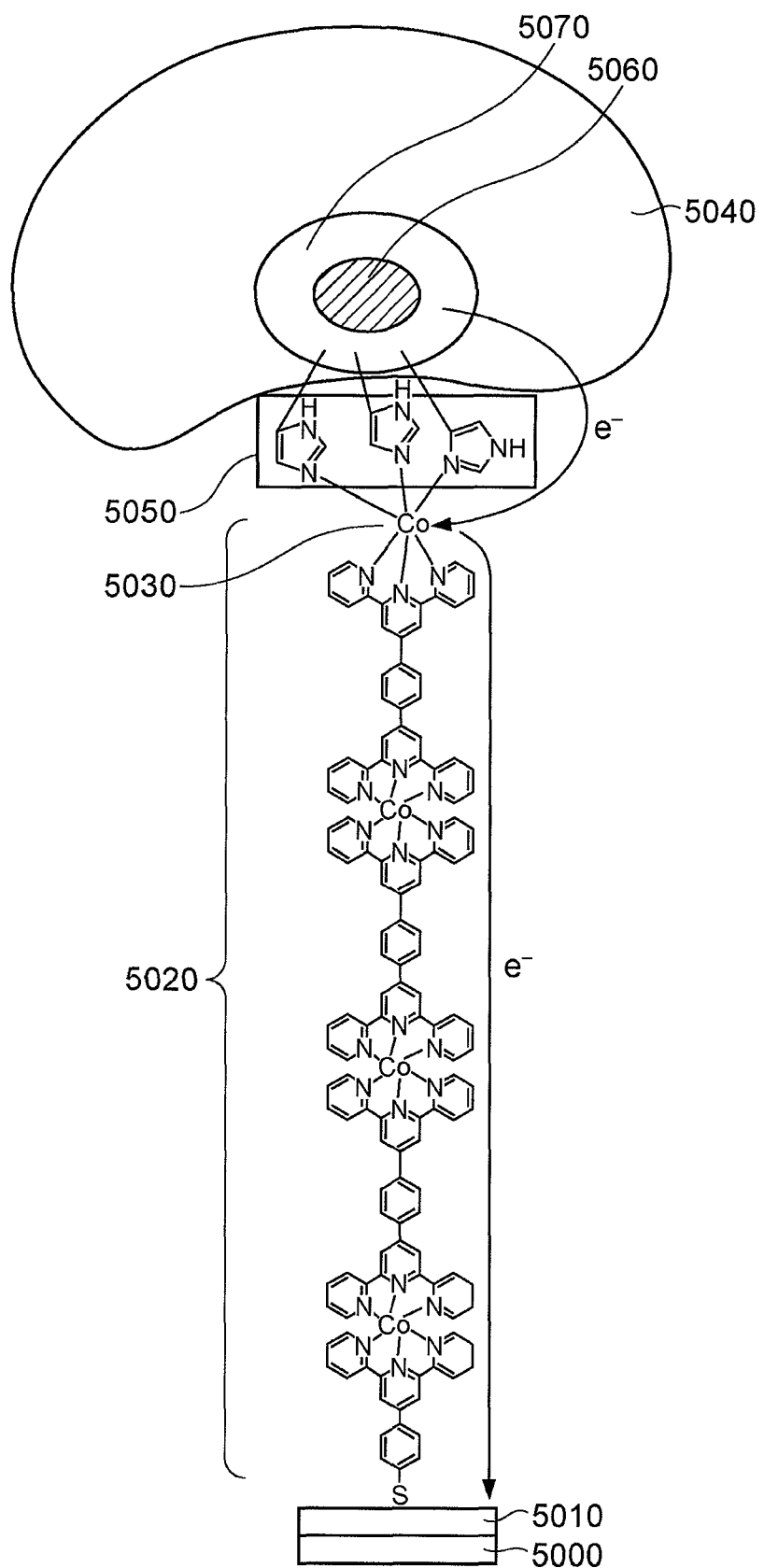
FIG. 5 is an illustration for explaining an enzyme electrode according to EXAMPLE 1 of the present invention.

FIG. 5 is a conceptual illustration of the enzyme electrode produced in EXAMPLE 1.

Referring to FIG. 5, a glass base plate 5000 and a gold electrode 5010 constitute an electrically conductive member. A cobalt complex 5020 is immobilized to the conductive member through gold/thiol binding. A histidine residue 5050 introduced to a molecule of *Armoracia rusticana* peroxidase 5040 is bound to cobalt 5030 at a terminal of the cobalt complex 5020. The histidine residue 5050 is introduced to a neighboring area 5070 of heme 5060 which serves as the active site of the *Armoracia rusticana* peroxidase 5040. Accordingly, electrons transferred to the heme through an enzyme reaction can be moved quickly to the conductive member through the cobalt complex.

In EXAMPLE 1, examples of the preparation of the enzyme electrode and the usage as a hydrogen peroxide sensor are described for each of the following items.

1. Synthesis of metallic complex ligand immobilized to electrode
2. Preparation of *Armoracia rusticana* peroxidase in which histidine is introduced to particular position
3. Preparation of Enzyme Electrode
4. Measurement of hydrogen peroxide

1. Synthesis of Metallic Complex Ligand Immobilized to Electrode

A description is now given of a method of synthesizing a complex ligand shown in following formula (1):

(Chemical formula 1)

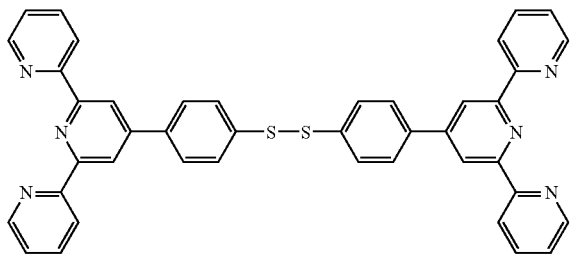

After adding, to equimolar ethanol solutions of 2-acetylpyridine and 4-methylthiobenzaldehyde, a 1.5-M aqueous solution of sodium hydroxide in half volume of the ethanol solutions to develop a reaction, an intermediate product is obtained through steps of filtering, cleaning with water and methanol, and drying.

Under a nitrogen atmosphere, 0.1 mL of 2-acetylpyridine is added to a tetrahydrofuran solution of potassium-tert-butoxide, and a mixture is stirred at room temperature. After adding 0.16 g of the above-described intermediate product to the mixture and developing a reaction at room temperature, ammonium acetate and ethanol are added in an excessive amount and a resulting solution is subjected to reflux. Then, the solution is evaporated under reduced pressure. A resulting product is washed with water and precipitated again from chloroform by using methanol. The ligand shown in formula (1) is thus obtained.

2. Preparation of *Armoracia rusticana* Peroxidase in which Histidine is Introduced to Particular Position A description is now given of the enzyme electrode produced by introducing histidine, i.e., the amino acid, to a particular position near the active site and coordinately binding the metallic complex to the introduced histidine.

From a seedling of *Armoracia rusticana*, cDNA is prepared in accordance with an ordinary method.

By using, as a template, the prepared cDNA and, as a primer, synthetic oligonucleotides, given below,

```
                                      [SEQ ID NO: 1]
5'-AATAATGGATCCCAACTTACCCCTACCTTCTACGACAATTCA-3'

(BamHI),
and

[SEQ ID NO: 2]
5'-AATAATCTCGAGAGAGTTGGAGTTCACCACCCTACAATTCAA-3'

(XhoI),
``` a PCR amplification reaction is performed to obtain an amplification product of about 920 base pairs.

By analyzing the DNA base sequence of the amplification product, it can be confirmed that the PCR amplification product [SEQ ID NO: 3] contains a gene (prxC1a) coding peroxidase which has the amino acid sequence expressed by SEQ ID NO: 4.

That DNA amplification product is cut by digestion using restriction enzymes BamHI and XhoI, and resulting DNA fragments of about 920 base pairs are inserted to the same sites as the restriction enzymes in pGEX-6P-1 (GE Healthcare Bio-Sciences Co.). A GST-fusion peroxidase expression vector pGEX-prxC1a is thereby produced.

A site specific variation is introduced to purified pGEX-prxC1a by using a commercially available kit, thus producing a variant peroxidase expression vector pGEX-mprxC1a.

The site specific variation introduced to the peroxidase gene is performed by selecting amino acids meeting all of the following conditions, and replacing each of the genes coding those amino acids with a gene coding histidine:

(1) In the amino acid sequence having peroxidase activity, the amino acid is positioned physically near heme, i.e., the site where electrons are transferred.

(2) The amino acid is positioned near the enzyme surface.

(3) Peroxidase activity of the enzyme is not reduced by the replacement of the amino acid with histidine.

(4) Binding to the metallic complex arranged outside the enzyme can be achieved with an imidazole group constituting a side chain of the substituted histidine.

A set of amino acids meeting the above conditions includes, for example, arginine 31, serine 73, and glutamine 176 in the amino acid sequence expressed by SEQ ID NO: 4. In such a way, histidine can be arranged near heme, which serves as the active site within the enzyme, at a distance of about 0.95 nm while controlling the position where histidine is arranged.

The replacement of those amino acids with histidine is performed by designing a primer and replacing bases in accordance with manuals attached to the commercially available kit.

The variant GST-fusion peroxidase expression vector pGEX-mprxC1a is transformed to *E. coli* BL21 (DE3) in accordance with an ordinary method. A resulting transformant can be selected as a resistant strain against antibiotic ampicillin.

The resulting transformant is pre-cultured in an LB medium added with antibiotic ampicillin. A part of the transformant is then added to an LB-Amp medium and cultured under shaking. After continuing the cultivation while adding IPTG, transformed bacteria are collected and suspended again in PBS. Then, a crude enzyme extract is obtained by crushing the bacteria and subjecting them to centrifugation.

GST-fusion peroxidase is purified from the crude enzyme extract by using Glutathione Sepharose beads. More specifically, Glutathione Sepharose is pre-treated so as to suppress non-specific adsorption by adsorbing BSA thereto in advance and is added to the crude enzyme extract under stirring, whereby GST-fusion peroxidase is adsorbed onto Glutathione Sepharose.

After the adsorption, Glutathione Sepharose is recovered through centrifugation and cleaned with PBS. Then, by adding Glutathione under stirring, adsorbed fused protein is eluted. After recovering a supernatant through centrifugation, GST-fusion peroxidase is purified by performing dialysis with respect to PBS. The purified GST-fusion peroxidase is digested by GST-fusion protease to be cut at the GST site. Then, the cut GST-fusion peroxidase is passed through Glutathione Sepharose to remove the GST-fusion peroxidase and GST. Further, by performing flow-through fractionation in a Sephadex G200 column which is equilibrated using PBS, a finally purified product of variant peroxidase is obtained which contains the amino acid sequence expressed by SEQ ID NO: 5.

The peroxidase activity can be determined as follows. For example, 2,2'-azino-di-[3-ethylbenzthiazoline-6-sulfonate] diammonium salt (ABTS) is used as a coloring substance.

Then, the peroxidase activity is determined by measuring a change of absorbance at 420 nm.

3. Preparation of Enzyme Electrode

A commercially available slide glass is ultrasonically cleaned in acetone and is dried in a flow of nitrogen gas. Titanium/gold are vapor-deposited on the slide glass in thickness of 20/200 nm, thus preparing an electrically conductive base plate. After cutting the base plate, the cut base plate is immersed in a 3/7-solution of a hydrogen peroxide solution/concentrated sulfuric acid for 20 minutes, followed by washing with water and drying in a flow of nitrogen gas.

(a) The base plate is immersed in a chloroform solution of the ligand expressed by formula (1). Thereafter, the base plate is cleaned with chloroform and is dried in a flow of nitrogen gas.

(b) Next, the base plate is immersed in an aqueous solution of cobalt chloride (II). Thereafter, the base plate is washed with water and is dried in a flow of nitrogen gas.

(c) Next, the base plate is immersed in a chloroform solution of 4',4''''-(1,4-Phenylene)bis(2,2':6',2''-terpyridine). Thereafter, the base plate is cleaned with chloroform and is dried in a flow of nitrogen gas.

By repeating the steps (b) and (c) in the order of (b)-(c)-(b)-(c)-(b), the metallic complex immobilized to the conductive base plate is obtained.

A buffer of *Armoracia rusticana* peroxidase to which histidine is introduced as described above is prepared and the conductive base plate including the immobilized metallic complex is immersed in the buffer, whereby the enzyme is immobilized to the metallic complex. An amount of the immobilized enzyme can be estimated, for example, by a quartz crystal microbalance method. Thereafter, the enzyme electrode is prepared by cleaning the conductive base plate and removing the enzyme which is not coordinately bound to the metallic complex.

Thus, the histidine arranged near the active site within the enzyme and the cobalt atom serving as the metal center of the metallic complex are coordinately bound to each other. As a result, the metallic complex functioning as a mediator can be arranged while the position thereof is controlled relative to the active site.

4. Measurement of Concentration of Hydrogen Peroxide

A 3-electrode cell is constituted such that the prepared enzyme electrode is a working electrode, a platinum wire is a counter electrode, and a silver/silver chloride electrode is a reference electrode. The 3-electrode cell is connected to a potentiostat, and a 0.1-M phosphoric acid buffer is used as the electrolyte. Prior to the measurement, by employing a hydrogen peroxide buffer with a known concentration and applying a potential of 500 mV vs. Ag/AgCl to the working electrode, a stationary current (enzyme current) is observed and a calibration curve is prepared. Then, by adding a material containing hydrogen peroxide with an unknown concentration to the electrolyte and applying the same potential, a stationary current is observed to measure the concentration of the added material.

Example 2

Figure 6:
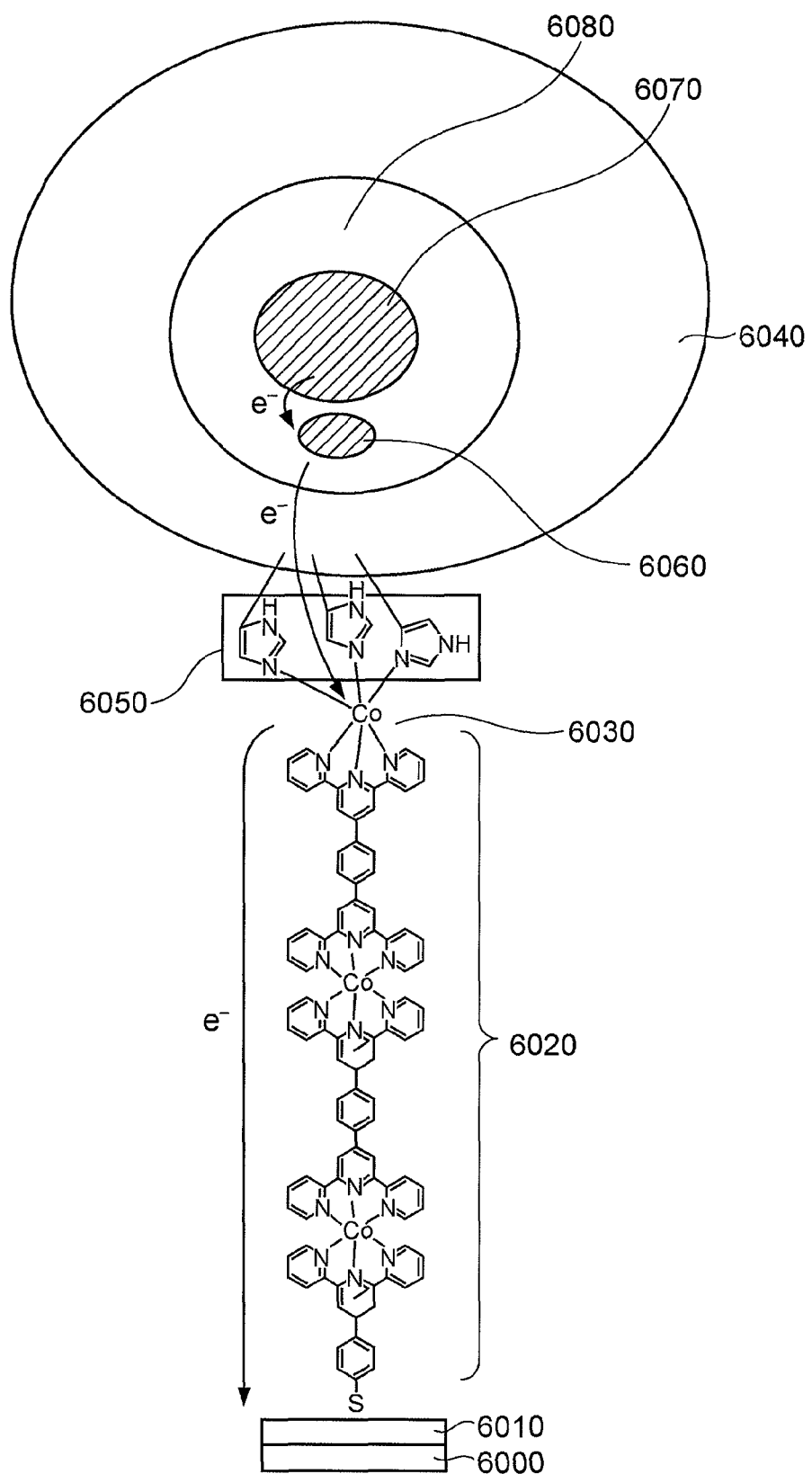
FIG. 6 is an illustration for explaining an enzyme electrode according to EXAMPLE 2 of the present invention.

FIG. 6 is a conceptual illustration of the enzyme electrode produced in EXAMPLE 2.

Referring to FIG. 6, a silicon base plate 6000 and a gold electrode 6010 constitute an electrically conductive member. A cobalt complex 6020 is immobilized to the conductive member through gold/thiol binding. A histidine residue 6050 introduced to a molecule of glucose oxidase 6040 is bound to cobalt 6030 at a terminal of the cobalt complex 6020. Another histidine to which a metallic complex is to be bound is introduced into the glucose oxidase. Reference numeral 6060 denotes the other histidine to which a cobalt complex is bound. The histidine 6060 to which the cobalt complex is bound is introduced to a neighboring area 6080 of FAD 6070 which serves as the active site of the glucose oxidase. Accordingly, electrons transferred to the FAD through an enzyme reaction can be moved quickly to the conductive member through the cobalt complex.

In EXAMPLE 2, examples of the preparation of the enzyme electrode and the usage as a glucose sensor and a biofuel cell are described for each of the following items.

1. Synthesis of metallic complex for immobilizing enzyme (i.e., cobalt complex constituting 6060)

2. Preparation of glucose oxidase in which histidine is introduced to particular position 3. Preparation of enzyme electrode 4. Measurement of glucose concentration 5. Operation of biofuel cell 1. Synthesis of the Metallic Complex for Immobilizing Enzyme A description is now given of a method of synthesizing a complex shown in following formula (2):

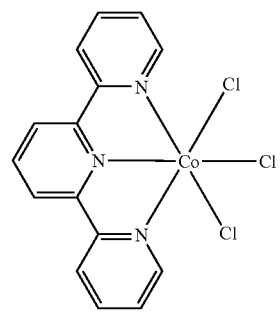

(Chemical formula 2)

Equimolar 2,2':6',2''-terpyridine and cobalt chloride (II) are reacted with each other in an ethylene glycol solvent by performing reflux in a nitrogen atmosphere. After air-cooling a reaction solution, the cooled solution is dripped into 500 mL of diethyl ether under strong stirring. A resulting precipitate is washed with water and diethyl ether, and is dried. The complex shown in formula (2) is thus obtained.

2. Preparation of Glucose Oxidase in which Histidine is Introduced to Particular Position Penicillium amagasakiense (ATCC 28686) is inoculated to an agar plate including a potato and glucose and is cultured at 25° C., thus obtaining cultured cells. After suspending the obtained cultured cells in a phosphoric acid buffer, the cells are recovered through centrifugation and are cleaned. From those cultured cells, cDNA is prepared in accordance with an ordinary method. By using, as a template, the prepared cDNA and, as a primer, synthetic oligonucleotides, given below,

```
                                                          [SEQ ID NO: 6]
5'-AATAATCATATGGCCTACCTGCCTGCCCAACAGATTGATGTCCA

G-3'(NdeI),
and
                                                          [SEQ ID NO: 7]
5'-AATAATCGGCCGCTAGGCACTTTTGGCATAGTCATCCAAAAT-3'

(EagI),
``` a PCR amplification reaction is performed to obtain an amplification product of about 1,700 base pairs.

By analyzing the DNA base sequence of the amplification product, it can be confirmed that the PCR amplification product [SEQ ID NO: 8] contains a gene coding glucose oxidase which has the amino acid sequence expressed by SEQ NO: 9.

That DNA amplification product is cut by digestion using restriction enzymes NdeI and EagI, and resulting DNA fragments of about 1,700 base pairs are inserted to the same sites as the restriction enzymes in pET-21a(+) (Novagen Co.). A glucose oxidase expression vector pET21-GOX is thereby produced.

A site specific variation is introduced to purified pET21-GOX by using a commercially available kit, thus producing a variant glucose oxidase expression vector pET-mGOX.

The site specific variation introduced to the glucose oxidase gene is performed as follows.

Amino acids meeting all of the following conditions (1) to (3) or (2) to (4) are selected, and genes coding those amino acids are each replaced with a gene coding histidine. If available, an amino acid meeting all of the conditions (1) to (4) by itself can also be selected.

(1) In the amino acid sequence having glucose oxidase activity, the amino acid is positioned physically near flavin adenine dinucleotide, i.e., the site where electrons are transferred.

(2) Glucose oxidase activity is not reduced by the replacement of the amino acid with histidine.

(3) The amino acid can form a complex with a metal atom through an imidazole group constituting a side chain of the substituted histidine.

(4) Of amino acids positioned near the enzyme surface, the relevant amino acid can be used for binding to the metallic complex arranged outside the enzyme when replaced with histidine.

Examples of a set of amino acids meeting the above conditions are as follows.

One example of the set includes threonine 108-aspartic acid 231-serine 61-glutamine 6 in the amino acid sequence expressed by SEQ ID NO: 9. Another example includes glycine 112-asparagine 221-serine 177-alanine 150. Still another example includes asparagine 111-aspartic acid 231-serine 61-glutamine 6.

In this EXAMPLE 2, a description is given of the case where four amino acids of threonine 108-aspartic acid 231-serine 61-glutamine 6 are replaced.

The replacement of those amino acids with histidine is performed by designing a primer and replacing bases in accordance with manuals attached to the commercially available kit.

The variant glucose oxidase expression vector pET-mGOX is transformed to E. coli BL21 (DE3) in accordance with an ordinary method. A resulting transformant can be selected as a resistant strain against antibiotic ampicillin.

The resulting transformant is pre-cultured overnight in an LB medium added with antibiotic ampicillin. A part of the transformant is then added to an LB-Amp medium and cultured under shaking. The cultivation is further continued while adding IPTG. IPTG-derived transformed bacteria are collected and suspended again in PBS. The bacteria are crushed by freeze-thawing and sonication and are subjected to centrifugation, thus obtaining solid foreign substances containing inclusion bodies. The solid foreign substances containing inclusion bodies are cleaned twice with a Tris-HCl buffer (pH 8.0) containing NaCl and EDTA, and are further cleaned with a Tris-HCl buffer (pH 8.0) containing Triton X-100. Then, contaminating protein is removed by cleaning with a urea solution, thus purifying the inclusion bodies.

The purified inclusion bodies are suspended in an 8-M urea solution containing dithiothreitol and are left to stand in an icy bath for solubilization.

The solubilized protein is put in a dialysis tube and is dialyzed for refolding with respect to a Tris-HCl buffer (pH 8.0) containing glutathione, glycerol, and FAD.

The refolded protein solution is subjected to centrifugation to remove aggregated protein. Protein contained in a supernatant is passed, for fractionation, through a gel filtration column which is equilibrated using a sodium acetate buffer (pH 6.0). By selectively taking out a glucose oxidase active fraction, a purified product of variant glucose oxidase containing the amino acid sequence expressed by SEQ ID NO: 10 is obtained.

The glucose oxidase activity can be decided, for example, by measuring an amount of hydrogen peroxide which is generated with oxidation of glucose in a sodium acetate buffer under an enzyme saturated condition at 25° C. Stated another way, the glucose oxidase activity can be determined by using, e.g., 2,2'-azino-di-[3-ethylbenzthiazoline-6-sulfonate]diammonium salt (ABTS) as a coloring substance, and measuring a change of absorbance at 420 nm.

3. Preparation of Enzyme Electrode

Titanium/gold are vapor-deposited on a silicon base plate in thickness of 20/200 nm, thus preparing an electrically conductive base plate. After cutting the base plate, the cut base plate is immersed in a 3/7-solution of a hydrogen peroxide solution/concentrated sulfuric acid for 20 minutes, followed by washing with water and drying in a flow of nitrogen gas.

(a) The base plate is immersed in a chloroform solution of the ligand expressed by formula (1). Thereafter, the base plate is cleaned with chloroform and is dried in a flow of nitrogen gas.

(b) Next, the base plate is immersed in an aqueous solution of cobalt chloride (II). Thereafter, the base plate is washed with water and is dried in a flow of nitrogen gas.

(c) Next, the base plate is immersed in a chloroform solution of 4',4''''-(1,4-Phenylene)bis(2,2':6',2''-terpyridine). Thereafter, the base plate is cleaned with chloroform and is dried in a flow of nitrogen gas.

By repeating the steps (b) and (c) in the order of (b)-(c)-(b), the metallic complex immobilized to the conductive base plate is obtained.

A buffer of glucose oxidase to which histidine is introduced as described above is prepared and the conductive base plate including the immobilized metallic complex is immersed in the buffer, whereby the enzyme is immobilized to the metallic complex. An amount of the immobilized enzyme can be estimated, for example, by a quartz crystal microbalance method. Thereafter, the enzyme not coordinately bound to the metallic complex is removed by cleaning the conductive base plate with a buffer. The enzyme electrode is then prepared by immersing the conductive base plate in a 0.1-M phosphoric acid buffer of the compound (2).

Thus, the histidine arranged near the active site within the enzyme and the cobalt atom serving as the metal center of the metallic complex are coordinately bound to each other. As a result, the metallic complex functioning as a mediator can be arranged while the position thereof is controlled relative to the active site.

4. Measurement of Glucose Concentration

A 3-electrode cell is constituted such that the prepared enzyme electrode is a working electrode, a platinum wire is a counter electrode, and a silver/silver chloride electrode is a reference electrode. The 3-electrode cell is connected to a potentiostat, and a 0.1-M phosphoric acid buffer is used as the electrolyte. If necessary, oxygen is removed from the solution by bubbling inert gas. Prior to the measurement, by employing a glucose buffer with a known concentration and applying a potential of 500 mV vs. Ag/AgCl to the working electrode, a stationary current (enzyme current) is observed and a calibration curve is prepared. Then, by adding a material containing glucose with an unknown concentration to the electrolyte and applying the same potential, a stationary current is observed to measure the concentration of the added material.

5. Operation of Biofuel Cell

A biofuel cell is constituted by using the prepared enzyme electrode as an anode and a platinum wire as a cathode. A load, e.g., a liquid crystal display apparatus, is connected to leads taken out from the anode and the cathode. When glucose serving as fuel and an electrolyte containing the enzyme are filled between the anode and the cathode, an electromotive force is generated and the liquid crystal display apparatus is operated.

ADVANTAGES OF EXAMPLES

In the enzyme electrodes of EXAMPLES described above, histidine capable of coordinately binding to a metallic complex is introduced by a molecular biological technique to a position near heme which serves the active site of *Armoracia rusticana* peroxidase, or near FAD which serves as the active site of glucose oxidase. By binding, to the introduced histidine, a cobalt complex containing chlorine in the form of a leaving group within a molecule, the cobalt complex functioning as a mediator is immobilized near the active site.

Compared with the known enzyme electrode using an enzyme in which a mediator is introduced into an enzyme molecule at random, therefore, electrons can be moved more quickly from the active site of the enzyme to mediator molecules.

Accordingly, in a system where electrons transport from the active center of the enzyme is in the rate-determining step of an enzyme reaction, the enzyme electrode of EXAMPLES can overcome the rate-determining step. As a result, an enzyme electrode can be obtained which shows a larger number of turnovers, a higher current value, a larger amount of accumulated charges than those in known systems. Such characteristics can be practically utilized as follows.

1. In a system where electron transport from the active center of the enzyme is in the rate-determining step of an enzyme reaction, i.e., in a system where the substrate concentration is high and a substrate diffusion process is difficult to achieve the rate-determining step, the enzyme electrode of EXAMPLES can provide a larger current. When the enzyme electrode is applied to, e.g., a sensor by utilizing such a characteristic, a sensor having a higher limit in the concentration measurable range can be provided. Also, when applied to a fuel cell, it is possible to provide a fuel cell which has a higher current density and a power density improved in proportion thereto.

2. With the enzyme electrode of EXAMPLES, the rate of electron transfer from the active center of the enzyme can be increased and a current value per molecule of the enzyme can be increased. In other words, a required current value can be achieved by using a smaller amount of the enzyme. Accordingly, an amount of the enzyme used can be reduced and the resource and the cost required for producing the enzyme electrode can be cut.

3. As mentioned above, with the enzyme electrode of EXAMPLES, the rate of electron transfer from the active center of the enzyme can be increased and a current value per molecule of the enzyme can be increased. In other words, a required current value can be achieved by using a smaller amount of the enzyme. Accordingly, in an enzyme immobilized electrode, if the electrode has the same density of the immobilized enzyme as that in a known electrode, an electrode area can be reduced while maintaining an output current value and a charge amount at constant. By utilizing such an advantage of a reduction in the electrode area, a background current can be reduced and a signal/noise ratio can be increased. Also, a device size can be reduced. Consequently, a sensor with less noise, a smaller-sized sensor, and a fuel cell can be obtained.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Patent Application No. 2006-226699 filed Aug. 23, 2006, which is hereby incorporated by reference herein in its entirety.

What is claimed is:

1. An enzyme electrode comprising:
   a redox enzyme;
   an electrically conductive member to which the redox enzyme is immobilized;
   an iron, cobalt, ruthenium, osmium, or chromium metallic complex electrically connected to the electrically conductive member; and
   an amino acid capable of binding to the metallic complex by a coordinate bond arranged at an active site within the redox enzyme or at a controlled position near the active site,
   wherein the amino acid is coordinately bound to the metallic complex.

2. The enzyme electrode according to claim 1, wherein a gene coding the redox enzyme is recombined by a genetic engineering operation and the amino acid is artificially introduced to or near the active site within the redox enzyme.

3. The enzyme electrode according to claim 1, wherein the amino acid is histidine.

4. An enzyme sensor comprising an enzyme electrode and a unit arranged to apply a voltage or a potential to the enzyme electrode, the enzyme electrode comprising:
   a redox enzyme;
   an electrically conductive member to which the redox enzyme is immobilized;
   an iron, cobalt, ruthenium, osmium, or chromium metallic complex electrically connected to the electrically conductive member; and
   an amino acid capable of binding to the metallic complex by a coordinate bond located at an active site within the redox enzyme or at a controlled position near the active site,
   wherein the amino acid is coordinately bound to the metallic complex.

5. A fuel cell comprising an enzyme electrode, a counter electrode, and an electrolyte arranged between the enzyme electrode and the counter electrode, the enzyme electrode comprising:
   a redox enzyme;
   an electrically conductive member to which the redox enzyme is immobilized;
   an iron, cobalt, ruthenium, osmium, or chromium metallic complex electrically connected to the electrically conductive member; and
   an amino acid capable of binding to the metallic complex by a coordinate bond located at an active site within the redox enzyme or at a controlled position near the active site,
   wherein the amino acid is coordinately bound to the metallic complex.

* * * * *